United States Patent
Lizzi et al.

(10) Patent No.: US 6,846,290 B2
(45) Date of Patent: Jan. 25, 2005

(54) ULTRASOUND METHOD AND SYSTEM

(75) Inventors: Frederic L. Lizzi, Tenafly, NJ (US); Jeffrey A. Ketterling, New York, NY (US); Robert Muratore, Huntington, NY (US)

(73) Assignee: Riverside Research Institute, New York, NY (US)

( * ) Notice: Subject to any disclaimer, the term of this patent is extended or adjusted under 35 U.S.C. 154(b) by 70 days.

(21) Appl. No.: 10/439,098

(22) Filed: May 14, 2003

(65) Prior Publication Data
US 2003/0216648 A1 Nov. 20, 2003

Related U.S. Application Data

(60) Provisional application No. 60/380,399, filed on May 14, 2002.

(51) Int. Cl.[7] .................................................. A61B 8/00
(52) U.S. Cl. ....................................................... 600/439
(58) Field of Search ................................. 600/407–472; 610/2, 3; 128/898.916; 73/625, 626; 367/7, 11, 130

(56) References Cited

U.S. PATENT DOCUMENTS

| | | | |
|---|---|---|---|
| 4,484,569 A | 11/1984 | Drillere et al. | 128/660 |
| 6,039,689 A | 3/2000 | Lizzi | 600/439 |
| 6,238,342 B1 | 5/2001 | Feleppa et al. | 600/437 |

*Primary Examiner*—Ali Imam
(74) *Attorney, Agent, or Firm*—Baker Botts LLP

(57) ABSTRACT

Diagnostic ultrasound is used to measure distance from a transducer to selected tissue structure. In one arrangement, the focal point of a high intensity focused ultrasound transducer is adjusted in accordance with measured distance to the selected tissue structure. In a second arrangement a transducer transport apparatus moves a transducer to maintain a selected distance from tissue structure.

16 Claims, 3 Drawing Sheets

ULTRASOUND METHOD AND SYSTEM

REFERENCE TO RELATED APPLICATION

This Application claims the benefit of Provisional Application Ser. No. 60/380,399, filed May 14, 2002.

BACKGROUND OF THE INVENTION

This invention was made in connection with work supported in part by a Bioengineering Research Partnership Grant 5R01 CA84588 from the National Cancer Institute and the National Heart, Lung and Blood Institute.

The present invention relates to systems for diagnosis or therapy using ultrasound. In particular the invention relates to systems which may use transducer assemblies of the type described in U.S. Pat. No. 4,484,569, which is assigned to the assignee of the present application, and which is incorporated therein by reference.

The U.S. Pat. No. 4,484,569 describes a transducer assembly that enables imaging of tissue and the application of High Intensity Focused Ultrasound (HIFU) by providing a diagnostic transducer that is mounted on a HIFU transducer and has a common radiation axis therewith.

In U.S. Pat. No. 6,039,689, which is assigned to the same assignee as the present application, and incorporated hereby by reference, there is described a HIFU transducer having segmented electrodes which allow steering or refocusing of the HIFU focal point by variation of the electronic signals applied to the electrode segments.

It is an object of the present invention to provide methods for ultrasound diagnosis and treatment wherein the transducer can be located or focused according to the tissue characteristics.

SUMMARY OF THE INVENTION

In accordance with the invention there is provided a method for ultrasonic treatment of tissue using a transducer assembly having a first diagnostic transducer and a second therapy transducer, each having a radiation axis with a known orientation with respect to each other, wherein the therapy transducer is arranged with adjustable focal distance. The transducer assembly is positioned using the diagnostic transducer to insonify tissue to be treated in the region of tissue structure. The tissue to be treated is insonified using the therapy transducer. Movement of the tissue with respect to the transducer assembly is detected using the diagnostic transducer, the focal distance of the therapy transducer is adjusted to compensate for detected tissue movement, and the tissue is further insonified using the therapy transducer with adjusted focal distance.

Movement of the tissue may be determined by measuring distance to the tissue structure using the diagnostic transducer. The insonifying may comprise providing pulses of ultrasonic radiation from the therapy transducer, and movement of the tissue may be determined by operating the diagnostic transducer in time periods between the pulses. The therapy transducer may be used to create a lesion in the tissue, and position of the lesion with respect to the transducer can be determined using the diagnostic transducer.

In accordance with the invention there is provided a method for guiding motion of an ultrasonic transducer. The transducer is transported in a first selected transducer path and operated to record data corresponding to the contour of at least one feature of tissue to be examined. The data is used to select a second transducer path having a selected distance from the contour. The transducer is transported along the second transducer path while further operating the transducer.

The first selected transducer path may be a linear path. The transducer may comprise a transducer assembly arranged for diagnostic and therapy ultrasonic operation, wherein the transducer is operated as a diagnostic transducer to record the data, and wherein the further operating comprises operating the transducer for therapy. A desired orientation of the transducer may also be determined from the data, and orientation of the transducer may be controlled to the desired orientation during transporting of the transducer along the second transducer path. The transducer may be transported along a plurality of first selected transducer paths to record two dimensional data representing a contour of the tissue feature, and the second transducer path may be determined to have a selected distance from the contour. Alternately, the transducer may be a scanning transducer for recording two dimensional data representing a contour of a tissue feature. A plurality of second transducer paths may be determined using the data representing a two dimensional contour.

In accordance with the invention there is provided apparatus for ultrasonic therapy. A transducer assembly includes a first diagnostic transducer and a second therapy transducer each having a radiation axis with a known orientation with respect to the other. The therapy transducer is responsive to at least two ultrasonic signals having the same frequency and variable phase with respect to each other, wherein variation of phase of said signals is effective to change the focal position of radiation therefrom. A diagnostic system is coupled to the diagnostic transducer for determining distance to a selected reflecting portion of tissue. A phase controller is responsive to signals from the diagnostic system for controlling phase of the at least two ultrasonic signals in response to a change in the distance to the selected portion of tissue.

In accordance with the invention there is provided apparatus for ultrasonic insonification of tissue having a tissue contour. A transducer is provided for insonifying tissue and mounted on a transport apparatus arranged to move the transducer in at least two directions, including a first direction toward and away from the tissue and a second direction generally transverse to said first direction. A diagnostic system determines distance of the tissue contour from the transducer and transport apparatus, as the transducer is moved in the second direction to thereby determine the tissue contour. A transport controller operates the transport apparatus to transport the transducer in the first and second directions to maintain a selected distance of the transducer from the tissue contour.

The transport apparatus can be further arranged to rotate the transducer about an axis perpendicular to the first and second directions, and the transport controller can be arranged to control the rotation to maintain a radiation axis of the transducer in a direction perpendicular to the tissue contour.

For a better understanding of the present invention, together with other and further objects, reference is made to the following description, taken in conjunction with the accompanying drawings, and its scope will be pointed out in the appended claims.

DESCRIPTION OF THE INVENTION

Figure 1:
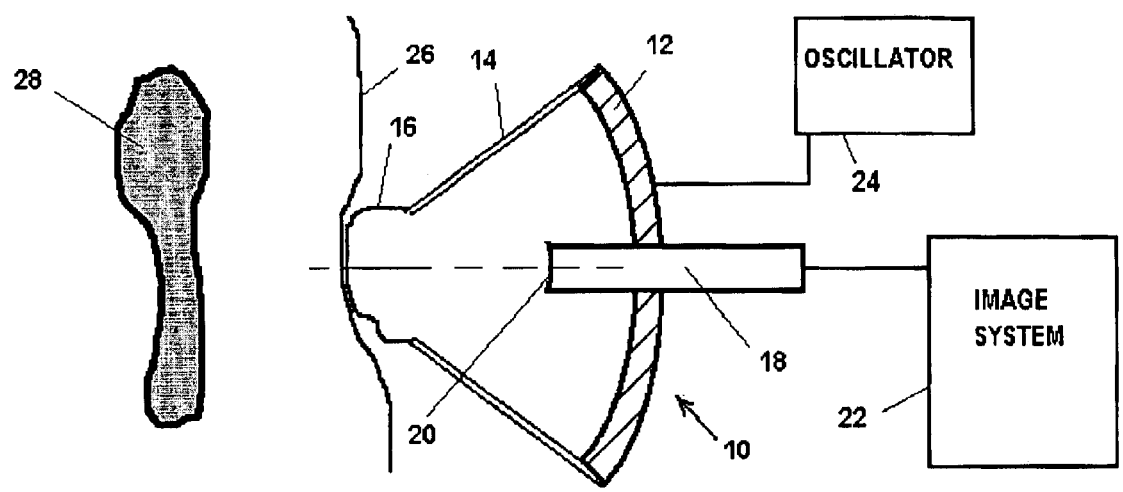
FIG. 1 is a diagram illustrating a configuration for practicing a first embodiment of the invention.
Figure 3:
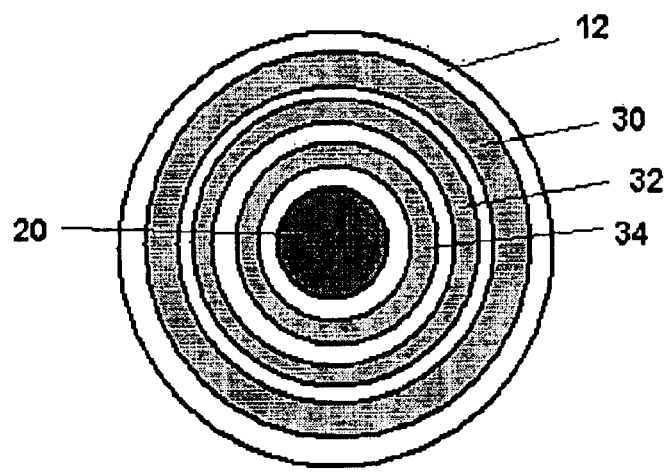
FIG. 3 is a frontal view of a transducer assembly useful for practice of the first embodiment of the invention.
Figure 4:
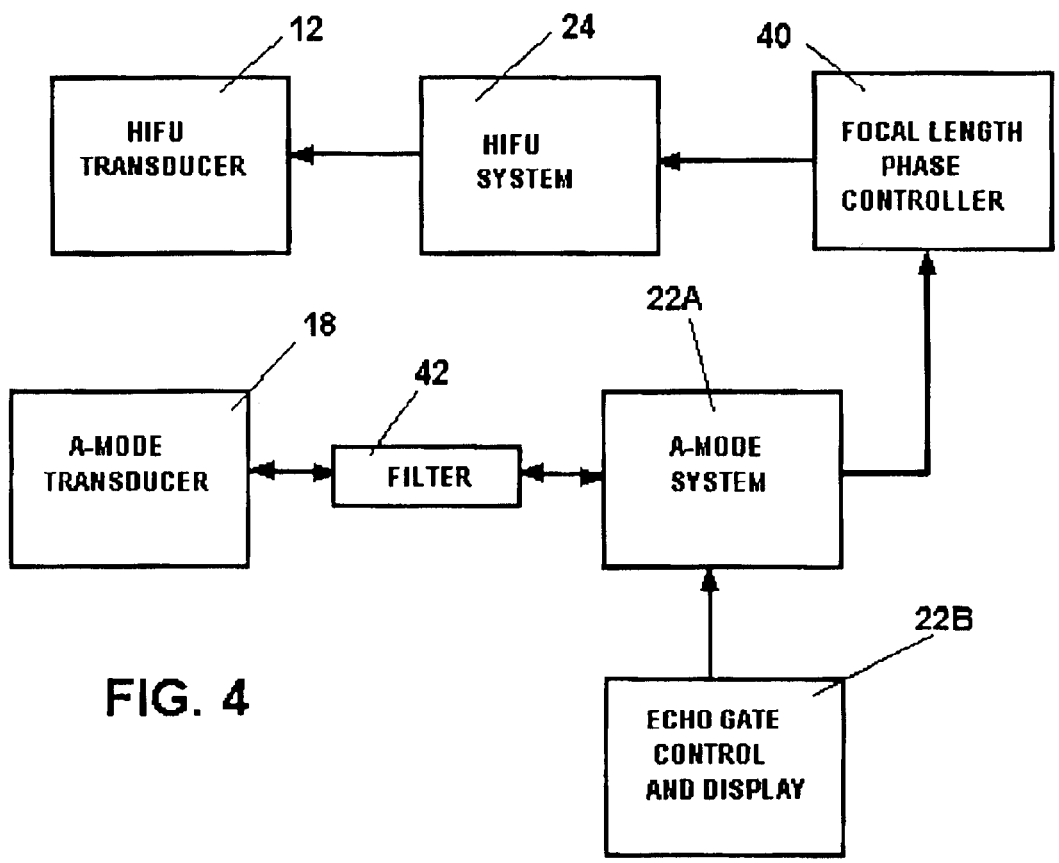
FIG. 4 is a block diagram of a system in accordance with an embodiment of the present invention.

Referring to FIGS. 1, 3 and 4 there is shown a first embodiment of a method and apparatus in accordance with the invention. FIG. 1 shows an exemplary clinical arrangement wherein it is desired to provide HIFU treatment to a region 28 of tissue which is separated from transducer assembly 10 by a tissue feature comprising boundary 26, which may be the skin of the patient. In some clinical situations the area around the region 28 of tissue may be subject to movement as may be caused by breathing of the patient, pulsatile blood flow or heart motion.

In the transducer assembly 10 depicted in FIG. 1, there is provided a diagnostic transducer 18 connected to diagnostic system 22, which may be an A-mode system. Transducer 18 has an aperture 20 and is mounted within piezoelectric shell 12 which forms a HIFU transducer for ultrasonic therapy. An example of such transducer assembly is described in referenced U.S. Pat. No. 4,484,569. Piezoelectric shell transducer 12 is mounted within coupling cone 14, which is typically filled with fluid for coupling ultrasonic signals to the patient's tissue. A flexible bladder 16 closes the opening of cone 14 and may be pressed against the skin 26 of a patient. Diagnostic system 22 may be any known type of imaging system operating on pulse-echo, A-mode or scanned B-mode, doppler imaging, contrast, harmonic imaging, or tissue analysis, as described in U.S. Pat. No. 6,238,342. The diagnostic transducer may alternatively be a one dimensional or two dimensional array for obtaining two or three dimensional image data.

As is well known, the piezoelectric shell transducer 12 provides ultrasonic radiation which converges to a focal point determined by the curvature of the spherical shell. U.S. Pat. No. 6,039,689, which is incorporated herein by reference, describes a piezoelectric shell transducer which has segmented electrodes on one or both the internal and external surfaces of the electrode. Providing phase shifted signals to the shell segment enables the direction of radiation of the transducer to be electronically steered, and in one example, to be refocused to a point close to or further from the natural focal point determined by the curvature of the shell.

Ultrasonic therapy relies on a high intensity of ultrasonic radiation within the area to be treated to enable the modification of the tissue thereat. Accordingly, focused ultrasonic energy has little effect on intervening tissue wherein the radiation passes through a larger cross section of tissue and has modifying effect near the focal point whereat the energy is concentrated in a small cross section.

If the tissue being treated moves, such as a result of the patient breathing or the patient's heartbeat or pulsating blood flow, the focal point of the HIFU transducer may be at a point that is in front of or behind the desired region of treatment. The system of FIGS. 1, 3 and 4 is arranged to modify the focal length of the HIFU transducer to compensate for tissue motion during treatment.

FIG. 3 is a view of the radiation surface of transducer shell 12 with cone 14 and bladder 16 removed. The surface includes concentric rings of metalization 30, 32 and 34 forming electrodes to which phase controlled signals to be radiated as HIFU waves are applied. Also visible is the radiating surface 20 of diagnostic transducer 18. By modifying the relative phase of signals applied to the metallized ring electrodes 30, 32, 34 of shell 12, the focal length can be modified to move the focal point toward or away from the shell. Those skilled in the art will recognize that it is equivalent, and in some cases may be advantageous, to place ring electrodes 30, 32, 34 on the exterior surface of shell 12. It will also be recognized that the number and size of the ring electrodes may be different than the example shown, and that the electrode segments may form a two dimensional array to provide beam scanning as well as focus control.

Referring to FIG. 4 there is shown a system for ultrasound treatment wherein movement of patient tissue is detected and compensated for by refocusing the HIFU transducer 12. A diagnostic imaging system 22 includes an A-mode system 22A and an echo gate control and display 22B connected to diagnostic transducer 18. The sub-units 22A and 22B make up image system 22 as shown in FIG. 1. The diagnostic imaging system is used to measure the distance to a feature of the tissue as it moves during insonification. The feature can be identified, for example, by manually placing an overlaid mark on the feature as displayed on the diagnostic image display using a computer interface device. The system tracks the distance to a tissue feature, such as skin 26 or a boundary of an organ, such as the heart. The diagnostic system 22 may utilize color-flow or power doppler techniques to locate tissues with respect to blood vessels or contrast agents may be injected to demarcate blood vessels. Tracking may use threshold algorithms or correlation analysis of sequential images. Since the diagnostic transducer is fixed in position with respect to the HIFU transducer 12 in transducer assembly 10, by knowing the distance of the tissue feature from transducer 18, the distance from transducer 12 and its natural focal point can be determined. In the case of tracking motion of skin 26, it may be assumed that the position of the region 28 of tissue to be treated is fixed with respect to skin 26. Alternately an internal feature, such as the wall of the heart or liver can be used to track motion.

Once position of the tracked tissue feature has been determined the treatment region at the focus of transducer 12 can be moved to compensate for the motion by adjusting phase and amplitude of signals supplied to rings 30, 32 and 34, thereby moving the focal point and treatment region. In addition, a lesion can be produced by the therapy ultrasound system and the image of the lesion used as a fiducial marker for tracking tissue movement and adjusting the focal length for subsequent treatment.

In one arrangement the HIFU is applied to the tissue in pulses, each pulse having a duration in the range of a few milliseconds. In this case the diagnostic system can be operated between HIFU pulses to avoid interference. Alternately, the HIFU insonification can be continuous and the diagnostic system provided with an optional filter 42 to prevent the HIFU signals from interfering with the diagnostic system receiver. Additionally, a single transducer may be used to perform the diagnostic and therapeudic insonifications.

Figure 2:
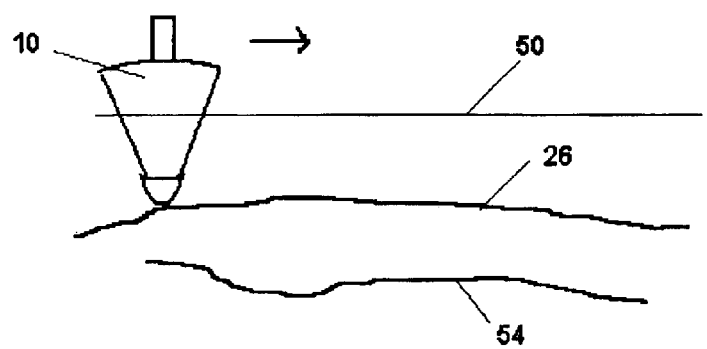
FIG. 2 is a diagram illustrating practice of a second embodiment of the invention.
Figure 5:
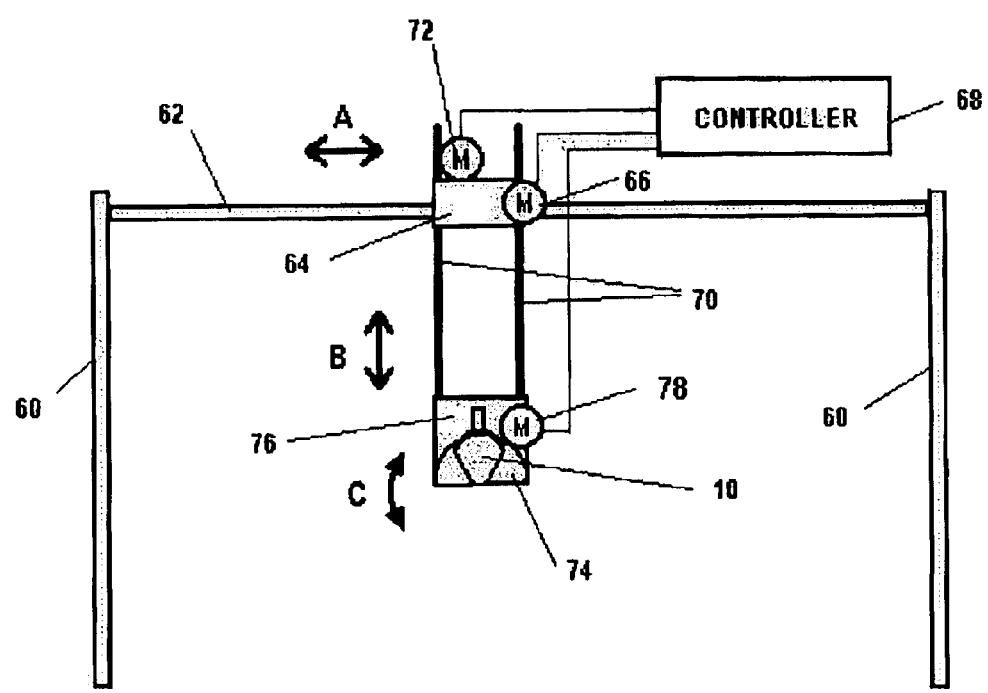
FIG. 5 is an elevation view of one arrangement of a transducer transport apparatus in accordance with an embodiment of the invention.

Referring to FIGS. 2 and 5 there will now be described a further embodiment of a method and apparatus in accordance with the invention. In the second embodiment the invention compensates for movement of the transducer instead of movement of the patient's body. In this embodiment the transducer assembly 10 as used in the first embodiment may also be used, but the second embodiment also encompasses systems that are purely diagnostic in nature and only include a diagnostic transducer 18. The object of the second embodiment is to maintain the focus of the transducer on a feature of the tissue while the transducer is moved across the tissue to obtain echo data, or to treat, a larger sample of tissue structure.

Referring to FIG. 2 there is shown a clinical arrangement wherein a transducer 10 is to be moved across an area of a patient's skin 26 in a path 50. In this case the transducer can be placed directly on the skin 26 or the patient may be immersed for examination in a bath which will conduct the ultrasonic signals. Also shown in FIG. 2 is a contour 54 which may be a boundary or feature of the tissue to be examined. Moving the transducer 10 in a straight line 50 for purposes of examination or treatment may not be desirable. It may be desired to move the transducer directly on or close to skin 26. Alternately it may be desired that the focal point of the transducer be maintained at, or a known distance from, a contour of tissue boundary or structure 54. Maintaining the focal point at a desired location within the tissue may be desired for treatment using HIFU or may be desired to improve imaging of the diagnostic system.

According to the invention, there is provided a method and apparatus wherein the transducer is moved in a first transducer path, such as a straight line 50, and data comprising distance to a contour or boundary is recorded. The contour or boundary can be specified by placing an overlay on the diagnostic image display using a computer interface device. Thereafter the transducer can be moved in a second transducer path which follows the contour detected in the first movement to maintain the transducer a constant distance from the a boundary contour or structure of interest. A third movement is also possible. For example in a first linear movement of the transducer, the surface of skin 26 is mapped. A second transducer path follows a path at a predetermined distance from skin 26 to detect internal structure, such as a blood vessel 54 to be imaged. In a third movement the transducer is maintained a fixed distance from the blood vessel to achieve superior imaging thereof or to effect HIFU treatment thereof.

In a preferred arrangement the transducer may be rotated about an axis to maintain the beam thereof in a direction that is perpendicular to the skin 26 or structure 54.

FIG. 5 depicts an exemplary apparatus for transporting a transducer along the first or second transducer path. A frame 60 supports a track 62 along which a carriage 64 is moveable in direction A using a motor 66. Carriage 64 carries vertical members 70 which are vertically moveable in direction B with respect to carriage 64 using motor 72. Vertical members 70 carry transducer mount 76. Transducer 10 is mounted on rotary member 74 on transducer mount 76 which rotates about an axis perpendicular to directions A and B using motor 78 to adjust the orientation of transducer 10 in rotational direction C. When the desired path and orientation of transducer 10 is determined by moving the transducer along a first transducer path, the determined contour of the tissue structure can be used to select a second transducer path at a selected distance from the contour. Transport controller 68 uses this data to operate motors 66, 72 and 74 to cause transducer 10 to follow the second transducer path.

Those skilled in the art will recognize that frame 60 can be moved in a direction perpendicular to directions A and B to obtain additional imaging or treatment scans of the tissue. Alternately, positioning information may be obtained if the imaging system incorporates a one or two dimensional array that provides two or three dimensional tissue information, which can be used to determine multiple transducer paths. Alternatively, a single transducer may be used to perform the diagnostic and therapeudic insonifications.

While there have been described what are believed to be the preferred embodiments of the invention, those skilled in the art will recognize that other and further changes and modifications may be made thereto without departing from the spirit of the invention, and it is intended to claim all such changes and modifications as fall within the true scope of the invention.

We claim:

1. A method for ultrasonic treatment of tissue, comprising:
providing a transducer assembly having a first diagnostic transducer and a second therapy transducer each having a radiation axis with known orientation with respect to each other, said therapy transducer being arranged with adjustable focal position;
positioning said transducer assembly to insonify tissue to be treated in a region of tissue structure using said diagnostic transducer;
insonifying said tissue to be treated using said therapy transducer;
determining movement of said tissue with respect to said transducer assembly using said diagnostic transducer; and
adjusting said focal position of said therapy transducer to compensate for said tissue movement and further insonifying said tissue using said therapy transducer with adjusted focal position.

2. A method as specified in claim 1 wherein said determining movement of said tissue comprises measuring distance to said tissue structure using said diagnostic transducer.

3. A method as specified in claim 1 wherein said insonifying comprises providing pulses of ultrasonic radiation from said therapy transducer, and wherein said determining movement of said tissue comprises operating said diagnostic transducer in time periods between said pulses.

4. A method as specified in claim 1 further comprising using said therapy transducer to create a lesion in said tissue, and wherein said determining movement of said tissue comprises determining position of said lesion with respect to said transducer assembly using said diagnostic transducer.

5. A method for guiding motion and orientation of an ultrasonic transducer, comprising:
transporting said transducer in a first selected transducer path and operating said ultrasonic transducer to record data corresponding to at least one feature of tissue to be examined;
determining from said data a second transducer path having a selected distance from said tissue feature; and
transporting said transducer along said second transducer path while further operating said transducer.

6. A method as specified in claim 5 wherein said first selected transducer path is linear.

7. A method as specified in claim 5 wherein said transducer comprises a transducer assembly arranged for diagnostic and therapy ultrasonic operation, wherein said transducer is operated as a diagnostic transducer to record said data, and wherein said further operating comprises operating said transducer for therapy.

8. A method as specified in claim 5 further comprising determining from said data a desired orientation of said transducer and wherein orientation of said transducer is controlled to said desired orientation during transporting of said transducer along said second transducer path.

9. A method as specified in claim 5 wherein said transducer is transported along a plurality of said first selected transducer paths to record two dimensional data representing a contour of said tissue feature, and wherein said determining of said second transducer path comprises determining said path to have a selected distance from said contour.

10. A method as specified in claim 9 wherein said determining said second transducer path comprises determining a plurality of second transducer paths.

11. A method as specified in claim 5 wherein operating said transducer to record data comprises recording two-dimensional data corresponding to a contour of said feature.

12. A method as specified in claim 11 wherein said determining said second transducer path comprises determining a plurality of second transducer paths.

13. Apparatus for ultrasonic therapy, comprising:
   a transducer assembly including a first diagnostic transducer and a second therapy transducer each having a radiation axis with known orientation with respect to each other, said therapy transducer being responsive to at least two signals having the same frequency and variable phase with respect to each other, said therapy transducer being responsive to variation of phase of said signals to change focal position of radiation therefrom;
   a diagnostic system coupled to said diagnostic transducer for determining distance to a selected reflecting portion of tissue; and
   a phase controller responsive to signals from said diagnostic system for controlling phase of said at least two signals in response to a change in said distance to said selected portion of tissue.

14. Apparatus for ultrasonic insonification of tissue having a tissue contour, comprising:
   a transducer for insonifying tissue;
   a variable transport apparatus carrying said transducer and arranged to move said tissue in at least two directions, including a first direction toward and away from said transducer and a second direction generally transverse to said first direction;
   a diagnostic system for determining distance of said tissue contour from transducer and said transport apparatus as said transducer is moved in said second direction to thereby determine said tissue contour; and
   a transport controller for operating said transport apparatus to transport said transducer in said first and second directions to maintain a selected distance of said transducer from said tissue contour.

15. Apparatus as specified in claim 14 wherein said transport apparatus is further arranged to rotate said transducer about an axis perpendicular to said first and second directions, and wherein said transport controller is arranged to control said rotation to maintain a radiation axis of said transducer in a direction perpendicular to said tissue contour.

16. Apparatus for ultrasonic therapy, comprising:
   a transducer assembly arranged to function as a diagnostic transducer and a therapy transducer for emitting diagnostic and therapy ultrasonic beams, each having a radiation axis with known orientation with respect to each other;
   a signal generator for supplying therapy signals to said transducer, said signal generator being responsive to control signals to change focal position of therapy radiation from said transducer;
   a diagnostic system coupled to said diagnostic transducer for determining position of a selected reflecting portion of tissue; and
   a controller responsive to signals from said diagnostic system for providing control signals in response to a change in said position of said selected portion of tissue.

* * * * *

UNITED STATES PATENT AND TRADEMARK OFFICE
CERTIFICATE OF CORRECTION

| | |
|---|---|
| PATENT NO. | : 6,846,290 B2 |
| APPLICATION NO. | : 10/439098 |
| DATED | : January 25, 2005 |
| INVENTOR(S) | : Lizzi et al. |

It is certified that error appears in the above-identified patent and that said Letters Patent is hereby corrected as shown below:

Column 1, lines 8-11; [Background of the Invention], first paragraph should be corrected as follows:

"This invention was made with government support in part by a Bioengineering Research Partnership under Grant 5R01 CA84588 awarded by the National Institutes of Health. The government has certain rights in the invention."

Signed and Sealed this
Twenty-eighth Day of August, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,846,290 B2 | Page 1 of 1 |
| APPLICATION NO. | : 10/439098 | |
| DATED | : January 25, 2005 | |
| INVENTOR(S) | : Lizzi et al. | |

It is certified that error appears in the above-identified patent and that said Letters Patent is hereby corrected as shown below:

Column 1, lines 8-11; [Background of the Invention], first paragraph should be corrected as follows:

"This invention was made with government support under Grant 5R01 CA84588 awarded by the National Institutes of Health. The government has certain rights in the invention."

This certificate supersedes the Certificate of Correction issued August 28, 2012.

Signed and Sealed this
First Day of January, 2013

David J. Kappos
*Director of the United States Patent and Trademark Office*